(12) United States Patent
Carlessi et al.

(10) Patent No.: US 8,927,770 B2
(45) Date of Patent: Jan. 6, 2015

(54) HIGH-YIELD PROCESS FOR THE SYNTHESIS OF UREA

(75) Inventors: Lino Carlessi, Dalmine (IT); Alessandro Gianazza, Legnano (IT)

(73) Assignee: Salpem, S.p.A., San Donato Milanese (MI) (IT)

( * ) Notice: Subject to any disclaimer, the term of this patent is extended or adjusted under 35 U.S.C. 154(b) by 0 days.

(21) Appl. No.: 14/116,258

(22) PCT Filed: May 3, 2012

(86) PCT No.: PCT/EP2012/058106
§ 371 (c)(1), (2), (4) Date: Nov. 7, 2013

(87) PCT Pub. No.: WO2012/152645
PCT Pub. Date: Nov. 15, 2012

(65) Prior Publication Data
US 2014/0081046 A1 Mar. 20, 2014

(30) Foreign Application Priority Data

May 10, 2011 (IT) .............................. MI2011A0804

(51) Int. Cl.
*C07C 273/04* (2006.01)
*C07C 213/04* (2006.01)

(52) U.S. Cl.
CPC ............. *C07C 273/04* (2013.01); *C07C 213/04* (2013.01); *B01J 2219/00024* (2013.01); *B01J 2219/00006* (2013.01)

USPC .................. 564/71; 564/66; 564/67; 564/69; 564/72

(58) Field of Classification Search
None
See application file for complete search history.

(56) References Cited

U.S. PATENT DOCUMENTS

| 3,662,521 | A | | 5/1972 | Behar et al. |
| 5,597,454 | A | * | 1/1997 | Lee .................................. 203/49 |
| 5,886,222 | A | * | 3/1999 | Rescalli .......................... 564/70 |
| 2010/0084350 | A1 | | 4/2010 | Liu et al. |

FOREIGN PATENT DOCUMENTS

| CN | 201596496 U | 10/2010 |
| CN | 201988375 U | 9/2011 |
| EP | 0111253 A2 | 6/1984 |
| EP | 1674449 A1 | 6/2006 |
| GB | 577581 A | 5/1946 |

* cited by examiner

*Primary Examiner* — Brian J Davis
(74) *Attorney, Agent, or Firm* — Tarolli, Sundheim, Covell & Tummino LLP

(57) ABSTRACT

A process for the direct synthesis of urea from ammonia and carbon dioxide at high pressures and temperatures, with the formation of ammonium carbamate as intermediate, comprising a decomposition step of the ammonium carbamate and stripping of the gases formed, operating substantially at the same pressure as the synthesis step, wherein the recycled liquid streams are fed, at least partially, to the same decomposition and stripping step after being preheated by heat exchange with a stream included in the high-pressure synthesis cycle.

11 Claims, 1 Drawing Sheet

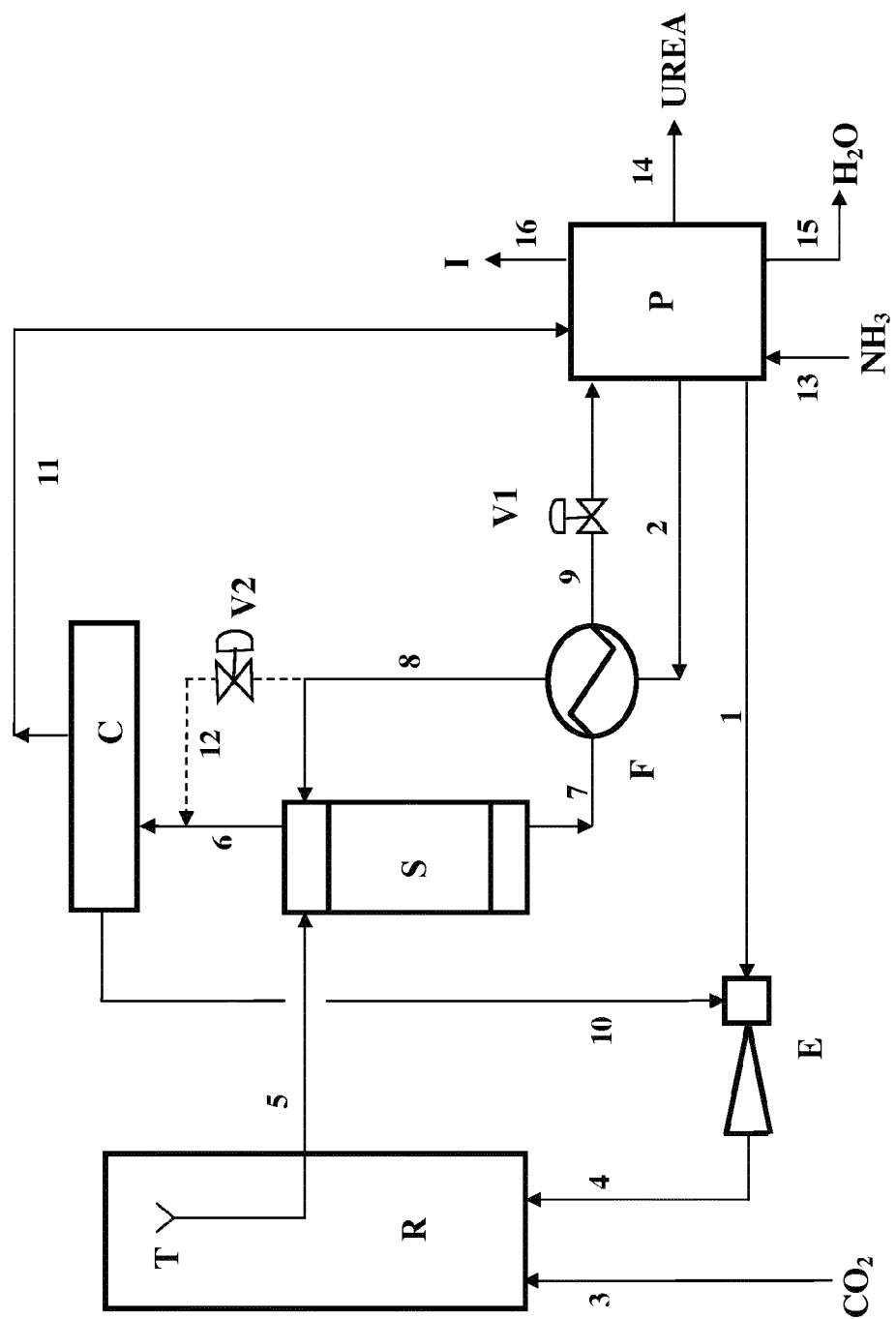

HIGH-YIELD PROCESS FOR THE SYNTHESIS OF UREA

FIELD OF THE INVENTION

The present invention relates to a high-yield process for the synthesis of urea.

In particular, the present invention relates to a total recycling process for the direct synthesis of urea starting from ammonia and carbon dioxide at high pressures and temperature, with an improved distribution of heat flows and matter, so as to produce a higher conversion of the reagents and a higher efficiency in the subsequent separation of urea from the reaction mixture and recycling of the non-converted reagents.

BACKGROUND

All industrial processes for the preparation of urea currently in use are based on direct synthesis according to the reaction:

$$2NH_3 + CO_2 \rightarrow CO(NH_2)_2 + H_2O \quad (1)$$

Which takes place in two separate reaction steps:

$$2NH_3 + CO_2 \rightarrow (NH_4)COONH_2 \quad (1a)$$

$$(NH_4)COONH_2 \rightarrow CO(NH_2)_2 + H_2O \quad (1b)$$

In the first step, there is an exothermic equilibrium reaction, kinetically favoured at room temperature, which however requires high pressures for reaching a favourable equilibrium at the high temperatures required in the subsequent step (1b).

In the second step, an endothermic reaction takes place, which reaches a significant rate only at high temperatures (>150° C.) with an equilibrium state which, at 185° C., leads to a conversion of only about 53% of the $CO_2$, in a mixture of the reagents in a stoichiometric ratio. This unsatisfactory conversion can be conveniently raised by increasing the $NH_3/CO_2$ ratio, but it is further reduced in the presence of water. The latter also has an unfavourable effect on the overall kinetics of the process.

The above two reaction steps do not normally take place in separate areas of the reactor, but contemporaneously in the reaction mixture, which therefore comprises urea, water, ammonia, carbon dioxide and ammonium carbamate, with a relative concentration, in the different points of the reactor, depending on the different thermodynamic and kinetic factors which contribute to the process.

Processes for the production of urea by direct synthesis starting from ammonia and carbon dioxide have been widely indicated and described in the specific literature of the field. A large review of the most common processes for the production of urea can be found, for example, in the publication "Encyclopedia of Chemical Technology" Ed. Kirk-Othmer, Wiley Interscience, fourth ed. (1998), Supplement, pages 597-621.

In industrial processes for the production of urea, the synthesis is normally carried out in a reactor fed with $NH_3$ and $CO_2$ and aqueous solutions of ammonium carbamate coming from the recycled streams of the non-converted reagents, at temperatures ranging from 170 to 200° C., at pressures not lower than 13 MPa, with a molar ratio $NH_3/CO_2$ ranging from 2.5 to 4.5, calculated on the sum of the feeding streams, also including the reagents present as ammonium carbamate. The $H_2O/CO_2$ molar ratio fed to the reactor, generally ranges from 0.5 to 0.6. Under these conditions, the product discharged from the reactor has conversions ranging from 50 to 65% with respect to the total $CO_2$ fed.

In addition to the water formed and excess of $NH_3$ fed, the effluent from the reactor still has considerable amounts of $CO_2$, mainly in the form of ammonium carbamate not converted to urea. The separation of urea from these products is effected, as is known, in various sections, operating at a high temperature and decreasing pressures, in which both the decomposition of the ammonium carbamate to $NH_3$ and $CO_2$ (products made available for recycling to the reactor) and the evaporation of the reaction water are effected, finally obtaining high-purity molten urea, sent to the final prilling or granulation step.

The separation and recycling section of the ammonium carbamate has investment and management costs which significantly affect the cost of the final product. From this section, all of the $CO_2$ and part of the $NH_3$, due to their contemporaneous presence, are made available for recycling as ammonium salts (carbonate and/or bicarbonate and/or carbamate, depending on the temperature and pressure) necessitating the use of water as solvent for their movement, in order to avoid the precipitation of the salts and the obstruction of the lines involved. This implies an increase in the amount of water present in the various liquid streams of the process and in the reactor, with the consequent negative effects on the conversion mentioned above.

Known processes which operate according to the above general scheme are described for example in U.S. Pat. No. 4,092,358, U.S. Pat. No. 4,208,347, U.S. Pat. No. 4,801,745 and U.S. Pat. No. 4,354,040.

In order to better clarify what is specified above, it should be pointed out that the amount of water recycled to the reactor for the above movement, is quantitatively in the order of that produced during the reaction. Traditional reactor is therefore particularly penalized as it is influenced, already in the feeding section of the reagents, by the high quantity of water coming from the recycled lines. Furthermore, the maximum water concentration is specifically in the terminal area of the reactor where, vice versa, it would be much more useful to have the lowest possible water concentration for favouring the shift of the equilibrium in step (1b) towards the right, specifically in this terminal area where the concentration of urea is already relatively high.

In order to overcome the above drawbacks and increase the conversion of $CO_2$ to urea as much as possible in traditional plants, attempts have been made to operate at even higher temperatures and pressures even if this implies a further increase in the investment and running costs. Even in this case however the conversion levels do not exceed 60-65%.

In published European patent application nr. 727414 (in the name of the Applicant), a process is described in which at least a part of the recycled stream of ammonium carbamate coming from the medium and low pressure sections, is sent directly to the separation/decomposition step (called stripping, according to the commonly used English notation) included in the high-pressure synthesis section of the process, so as to be decomposed into ammonia and carbon dioxide, separated as gaseous stream, whereas most of the water remains in the liquid stream at the outlet of the stripper. This solution has effectively allowed the conversion to be increased per passage in the reactor, reducing the amount of water present, but to the detriment of the thermal balance of the stripping step, which requires an additional amount of heat to evaporate the liquid stream of the recycled carbamate.

This can lead to an increase in the overall energy consumption and, in some cases, the necessity of modifying the equipment used for the stripping.

There is therefore still a considerable need for improvement in the production technology of urea suitable for making the synthesis process more efficient and economical.

BRIEF DESCRIPTION OF THE DRAWINGS

FIG. 1 schematically represents the embodiment represents the embodiment of the reaction and decomposition-stripping steps (synthesis loop) of a process for the synthesis of urea.

DETAILED DESCRIPTION

The Applicant has now found a modified process which allows the difficulties and limitations of the industrial processes mentioned above to be simply and effectively overcome, allowing $CO_2$ conversions to urea of over 70% to be reached, without requiring significant additional thermal supplies to the stripping step.

A first object of the present invention therefore relates to an improved process for the synthesis of urea from ammonia and carbon dioxide with the formation of ammonium carbamate as intermediate, comprising the following steps:

a) reacting ammonia and carbon dioxide as such or in the form of ammonium carbamate, with a $NH_3/CO_2$ molar ratio ranging from 2.3 to 6, preferably from 3.0 to 5.0, at temperatures ranging from 140 to 215° C. and pressures ranging from 12 to 25 MPa, with the formation of a first liquid mixture containing urea, ammonium carbamate, water and ammonia;

b) feeding said first liquid mixture to a decomposition-stripping step to effect the decomposition of at least an aliquot, preferably from 50 to 99%, of the ammonium carbamate into ammonia and carbon dioxide, substantially operating at the same pressure as said reaction step (a) and at temperatures ranging from 160 to 240° C., simultaneously subjecting said liquid mixture to stripping with the formation of a first gaseous mixture containing ammonia and carbon dioxide, and a second liquid mixture containing urea, water, ammonia and ammonium carbamate;

c) condensing at least 50% of said first gaseous mixture in a condensation step, substantially operating at the same pressure as said step (a), with the formation of a third liquid mixture containing ammonium carbamate, ammonia and possibly urea, directly or indirectly fed to the reaction step (a);

d) recovering the urea contained in said second liquid mixture in one or more consecutive decomposition and separation steps (P), with the formation of a fourth liquid mixture containing water, ammonia and ammonium carbamate and, possibly, a liquid phase substantially containing ammonia;

e) feeding at least a part of said fourth liquid mixture formed in step (d), preferably from 50 to 100%, to said decomposition-stripping step (b), sending the part possibly remaining to said reaction step (a), or, preferably, to said condensation step (c);

characterized in that said fourth liquid mixture either totally or partially fed to said decomposition-stripping step (b), is preheated by heat exchange with any of the above mixtures formed in steps (a), (b) or (c).

According to the process of the present invention, which is preferably carried out in continuous in an industrial plant, fresh ammonia and carbon dioxide are continuously fed to the plant to balance the corresponding amount of reagents converted to urea, which is removed at the outlet of the process, usually in solid form, as obtained in the final granulation or "prilling" section, or also in the form of a concentrated solution. Steps a), b) and c) belong to the so-called "high-pressure synthesis loop of urea" and are well known to experts, in the different variants published in the literature of this field.

The fresh ammonia and carbon dioxide, after compression to the desired reaction pressure, can be fed directly to the reactor, but at least one of these is preferably used, at least partly, as driving fluid in one or more ejectors, to provide the necessary drive for making the fluids circulate in the synthesis cycle, for example said first gaseous stream discharged from the decomposition-stripping step b) and/or the concentrated solution of ammonium carbamate coming from the condensation step c) and fed to the reactor. Liquid ammonia is particularly preferred to be used for this purpose.

Alternatively, or contemporaneously with use in the ejectors, the fresh ammonia or carbon dioxide can be used, totally or partly, as stripping fluid in the stripper and/or sent directly to the condenser.

The reaction step a) is normally carried out at temperatures ranging from 140 to 215° C., preferably from 170 to 205° C. and pressures ranging from 12 to 25 MPa, preferably from 14 to 18 MPa, with molar ratios of ammonia/carbon dioxide preferably ranging from 3.0 to 5.0, more preferably from 3.0 to 4.3. Suitable synthesis reactors are normally used, prepared for resisting the high temperatures and pressures of the reaction step and constructed with suitable materials and techniques for resisting the strong corrosive action of the reaction mixture. The synthesis reactor is preferably equipped with various plates, selected from the different types known in the art, so as to obtain optimal plug-flow regime conditions, optionally also in the presence of biphasic systems. The reactor can also include several reaction areas, suitably interconnected with each other, possibly having different feeding streams at different heights.

The heat developed, and more generally, the thermal level of the reactor in step a) can be controlled by acting on the thermal level of the streams of carbon dioxide or ammonia fed to the reactor, for example by distributing the same feeding streams between the stripper, condenser and reactor, as mentioned in the references of the art cited above, or, as indicated hereunder, also using the preheating of said fourth liquid mixture.

The reactor must have a hold-up liquid which is such as to allow a residence time of the same ranging from a few minutes to several tens of minutes to allow the ammonium carbamate formed by reaction of ammonia with carbon dioxide in the condensation step (c) and/or in the reactor itself, to dehydrate to urea.

In the process according to the invention, in the reaction step (a), a further gaseous stream rich in inert products to be discharged, can also be separated, if necessary, at the outlet of the head of the reactor. This gaseous stream is preferably subjected to condensation in the separation and purification section to recover the ammonia and carbon dioxide contained therein, which are recirculated together with the other recycled streams of the present process. In a second embodiment, this additional gaseous stream is sent to the decomposition-stripping step, from which the inert products are transferred, with the other gaseous components, to the condensation step (c), and from here, are separated, emerging either directly from the condenser (C), or from a subsequent separation step inserted in the separation and purification section analogously to the previous case.

In the process according to the present invention, operating in the reactor with an excess of ammonia with respect to the stoichiometric ratio with carbon dioxide, the stream leaving the reactor and, in general, most of the liquid mixtures (or streams) which are formed in the process, usually contain ammonia in excess. During the present description, reference is made to the composition of these streams and liquid mixtures (or also biphasic) conventionally considering that all the carbon dioxide is present in the form of ammonium carbamate, and the remaining excess of ammonia is present as free ammonia, or more simply ammonia.

Finally, in order to simplify the present description, the term "liquid" is used indifferently with reference to streams or mixtures of the process according to the present invention, which consist of either a single liquid phase or a mixed liquid-vapour phase. The term "gaseous", on the other hand, is used for those streams or mixtures in which the liquid phase is substantially absent.

Said first liquid mixture, formed in the reaction step (a), is transferred, with suitable ducts, to the decomposition-stripping step (b), where it is kept at a high thermal level, preferably at a temperature ranging from 5 to 50° C. higher than that at the outlet of the reaction step, usually supplying the heat necessary for decomposition and the formation of the gaseous phase using high-pressure indirect vapour. The decomposition-stripping step (b) is normally carried out in a suitable apparatus, called stripper, substantially consisting of a heat exchanger of the vertical falling type. The temperature of the stripper normally ranges from 160 to 240° C., whereas the pressure is equal to or slightly lower than that of the reactor, thus allowing the recirculation of the decomposition products (first gaseous stream) using, as movement means, exclusively, and possibly, ejectors rather than pumps.

Under the above conditions, the ammonium carbamate which has not been converted to urea, present in the first liquid mixture, tends to rapidly decompose forming ammonia and carbon dioxide, whereas the urea already formed in the reactor substantially remains unaltered (losses normally less than 2% with respect to the total). The stripping can be carried out using fresh ammonia or carbon dioxide as carrier gas. Various examples of processes for the synthesis of urea using the above principle are described in literature. U.S. Pat. No. 3,356,723, for example, describes the use of carbon dioxide as stripping gas whereas patent GB 1.016.220 describes the use of ammonia for the same purpose.

In a preferred embodiment of the present invention, the decomposition-stripping step (b) is carried out using, as carrier gas, the same ammonia present in excess in the liquid stream leaving the reactor. In this case, it is preferable to operate in the reaction step with a $NH_3/CO_2$ ratio ranging from 3.1 to 5. Further details on this preferred technology can be found, for example in U.S. Pat. No. 3,876,696. This latter technology is indicated with the term "self-stripping". In the latter case, the thermal control of the stripper is critical and the advantages of the present invention are particularly evident.

According to the present invention, a first gaseous mixture of ammonia and carbon dioxide is obtained from the decomposition-stripping step (b), having a very low water content (as vapour), normally lower than 20%, preferably ranging from 2 to 15% by weight, with respect to the overall weight of the gaseous mixture. This low water content is in accordance with what is normally obtained in the high-pressure stripping operations effected according to the processes previously indicated.

The decomposition-stripping step (b) is generally carried out in equipment (stripper) consisting, for example of falling liquid film tube-bundle heat exchangers, whose characteristics, in the various possible variants, are well-known to experts in the field. The mixture leaving the reactor, together with the fourth liquid mixture coming from the purification steps downstream of the stripper, is preferably fed to the head of the apparatus and forms a film falling onto the walls of the tube bundle. Said first and fourth liquid mixture can be fed separately to the head of the stripper, or they can be joined by sending them into a single feeding line.

The condensation step (c) is normally carried out in suitable condensers, for example, tube-bundle or surface condensers, in which the condensation heat is removed by heat exchange with other fluids, preferably for the production of vapour.

According to the present invention, the condensation step can be carried our under the usual conditions (temperature, pressure and composition) used in the known processes, provided these are such as to prevent the formation of solid ammonium carbamate in the condenser or lines leaving this. The third liquid mixture formed in step (c) is preferably at a temperature ranging from 140 to 170° C., preferably from 150 to 160° C.

The separation of urea from the ammonia and ammonium carbamate still present in the second liquid stream leaving the decomposition-stripping step, is effected, according to step (d) of the present process, in consecutive decomposition and separation sections, operating at medium pressure (from 1.5 to 2.5 MPa) or low pressure (from 0.3 to 1.0 MPa). For the purposes of the present invention, said separation step (d) can be effected using any of the methods described in specific literature of the field, which allow to obtain a recycled liquid stream containing an aqueous solution of ammonium carbamate and ammonia, and possibly also a stream essentially consisting of ammonia. Separation and purification sections suitable for the purposes of the present invention are, for example, those schematically represented in FIGS. 1 to 5 of the publication "Encyclopedia of Chemical Technology" cited above.

The urea thus separated from the ammonium carbamate and ammonia is generally obtained as an aqueous solution which is subjected to a final dehydration step under vacuum (up to 1 KPa), obtaining water on the one hand, and substantially pure urea on the other, sent to normal prilling, granulation processes, etc.

The separation and purification step (d) of urea, according to the present invention, also comprises the final dehydration step and purification section of the wastewater leaving the synthesis plant. According to a preferred embodiment of the present invention, the various streams containing $CO_2$ and $NH_3$, liquid or biphasic, coming from the various subsections of step (d) (medium- and low-pressure decomposition of the carbamate, recondensation of the carbonate and/or carbamate, dehydration of the urea, purification of the wastewater), are joined in a single recycled stream which forms said fourth liquid mixture, which is then fed, either totally or partially, to the first decomposition-stripping step according to step (e) of the present process.

In accordance with what is known in the art with respect to the equilibriums which regulate the composition of the aqueous solutions of ammonia and carbon dioxide, the fourth liquid mixture of the present invention can contain carbonate, bicarbonate and ammonium carbamate, or a mixture thereof, depending on the temperature and pressure of the mixture itself. At high pressures and temperatures of the urea synthesis cycle, said fourth liquid mixture is substantially composed of an aqueous solution preferably containing from 25 to 40% by weight of ammonium carbamate and from 30 to 45% by weight of free ammonia, the remaining percentage essentially consisting of water. The relative quantity of said fourth recycled liquid mixture normally represents from 25 to 35% by weight with respect to said second liquid mixture leaving the stripper and mainly depends on the conversion efficiency in the reactor of step (a) and/or decomposition of ammonium carbamate in step (b).

According to the present invention, said fourth liquid mixture is preheated before being fed to the high-pressure decomposition-stripping step (b), by means of heat exchange with a fluid having a higher thermal level present in one of steps (a), (b) or (c) of the synthesis loop. A fluid stream formed in step (b) is preferably used, having the highest thermal level, for example said first gaseous mixture or, more preferably, said second liquid mixture leaving the same step (b).

Possibly, only the part of said fourth liquid mixture which is fed to the decomposer-stripper is preheated, whereas the part fed to the condenser or directly to the reactor maintains the original thermal level.

The heat exchange necessary for preheating the fourth liquid mixture can be obtained with any heat exchanger suitable for the purpose and adequately dimensioned, such as, for example, a tube-bundle exchanger, circulating one mixture on the shell side and the other, preferably that having a higher temperature, on the tube side.

In accordance with the present invention, the variation in temperature of said fourth liquid mixture in the preheating preferably ranges from 30 to 140° C., more preferably from 60 to 130° C., whereas the initial temperature of the same mixture at the inlet of the heat exchanger preferably ranges from 70 to 120° C. and that at the outlet from 130 to 220° C.

If the preheating of the fourth liquid mixture is effected by exchange with said first gaseous mixture leaving the stripper, the latter is either totally or partly condensed, forming a liquid mixture comprising ammonium carbamate. In this case, therefore, at least a part of said condensation step (c) and the preheating step are preferably carried out in the same equipment which represents an exchanger/condenser into which said first gaseous mixture flows and preferably condenses at the shell side and said fourth liquid mixture flows and is heated at the tube side.

In the preferred embodiment, said second liquid mixture leaving the decomposition-stripping step, whose temperature generally ranges from 160 to 240° C., preferably from 180 to 220° C., is used as heating mixture or stream.

In a further embodiment, before being fed to the decomposition-stripping step, said fourth liquid mixture can be preheated by passing it into a tube or coil immersed in the reaction mixture inside the reactor itself, so that it can act as cooling fluid in the hotter areas of the reactor and prevent undesired overheating which can favour, for example, corrosion and the formation of biuret.

The application of other partial heating methods of the fourth liquid mixture (up to 50% of the overall heat requirement), in addition to those mentioned above, such as for example, the use of oversaturated vapour or high-temperature water coming from the condensation of high-pressure vapour in the stripper used for effecting step (b), is however not excluded from the scope of the present invention, which, under certain circumstances and variants of the process, can favour reaching the desired feeding temperature to the stripper-decomposer. This therefore facilitates the overall thermal regulation of the process and relative plant, with particular reference to maintaining a sufficient thermal level of the second liquid mixture after passage in the heat exchanger, sufficient for sustaining the subsequent expansion in the medium-low pressure decomposition and separation step (d).

The process according to the present invention allows the quantity of water fed to the reactor to be significantly lowered to a level which is such as to have a $H_2O/CO_2$ molar ratio at the inlet lower than 0.40, preferably ranging from 0.10 to 0.35, more preferably from 0.15 to 0.25 (wherein the $CO_2$ in the reactor is conventionally in the form of carbamate, as previously specified), without however encountering the drawbacks observed in the practical embodiment of the synthesis process of urea according to what is disclosed in patent application EP nr. 727414 mentioned above.

In this way, the synthesis of urea is effected with particularly high conversions, preferably ranging from to 75% per passage, without having to resort to particularly complex and onerous technical solutions, at the same time maintaining a sufficient thermal level in the decomposition-stripping step, whether the stripping be effected with the supply of a gas specifically fed, or, in particular, in the case of self-stripping using the excess ammonia leaving the reactor.

The present process also has the advantage of being able to be easily and surprisingly effected with a few simple modifications to an already existing traditional plant, provided this is equipped with a high-pressure stripping step. In particular, it is sufficient to modify the plant so as to send to said step of stripping step either all or part of the stream containing the recycled carbamate coming from the steps downstream of the stripper itself.

Another object of the present invention therefore relates to a method for improving the yield of an existing process for the production of urea, which operates with a high-pressure synthesis section comprising at least one (self)stripping step from which a liquid stream containing urea is obtained, together with a gaseous stream containing ammonia and carbon dioxide, and consecutive purification and concentration steps of the urea, from which a recycled aqueous solution containing ammonium carbamate is obtained, wherein said aqueous solution is fed, either totally or partially, preferably from 50 to 100%, to said (self)stripping step, characterized in that said aqueous solution is preheated by means of heat exchange with said liquid stream containing urea or said gaseous stream before being fed either totally or partially to said (self)stripping step.

A further object of the present invention also relates to a method for modifying a pre-existing plant for the direct synthesis of urea from ammonia and carbon dioxide comprising:

a high-pressure synthesis loop comprising a reactor R, a decomposer-stripper S, a condenser for the formation of ammonium carbamate C, a medium-low pressure section P for the separation and purification of urea, a fluid connection line L1 for sending recycled ammonium carbamate at a temperature T1 to said decomposer-stripper S;

a fluid connection line L2 for sending a liquid stream at a temperature T2>T1 (ΔT preferably ranging from 60 to 140° C.), comprising urea, water and residual ammonium carbamate to said section P;

characterized in that a heat exchanger F is positioned so as to effect a heat exchange between the fluids in said lines L1 and L2, with no contact between the same fluids.

The plant thus modified allows the synthesis process of urea to be carried out in accordance with claim 1.

The improved process according to the present invention is further illustrated by FIG. 1 enclosed, which schematically represents the embodiment of the reaction and decomposition-stripping steps (synthesis loop) of a process for the synthesis of urea, which is a preferred embodiment of the present invention.

In FIG. 1, the dashed lines represent alternative possibilities, not mutually exclusive, for effecting the process of the present invention. Excluding the valves V1 and V2 and ejector E, other functional details such as pumps, valves, and other equipment not significant for a complete understanding of the processes schematized, are not shown in FIG. 1.

In no case should the process according to the present invention be considered as being limited to what is indicated and described in the enclosed FIG. 1, which has a purely illustrative function of the invention.

The scheme indicated in FIG. 1 illustrates the reactor R which is connected, through the overflow T and line 5, with the stripper S. Line 7 sends the semi-purified mixture containing urea from the bottom of the latter through the heat exchanger F, from which the same mixture is then sent to the separation and purification section of urea P through line 9, on which the depressurization valve V1 is inserted. The solution of recycled ammonium carbamate is sent from the section P, through lines 2 and 8, and through the exchanger F, to the stripper S, and possibly part of it is sent directly to the condenser C through line 12 and the valve V2. Line 6 coming from the head of the stripper S, carrying the mixture of vapours generated in the high-pressure stripping step, is connected to the condenser C. The outlet of the condenser C is represented by line 10 that then connects to the reactor R, through the ejector E, to which the ammonia coming from the separation and purification section P of urea, comprising both recycled ammonia and fresh make-up ammonia fed to P by means of line 13, is also sent, as driving fluid, through line 1. The resulting mixture, leaving the ejector E, is fed through line 4 to the bottom of the reactor, to which line 3 which feeds fresh carbon dioxide, is also connected. The possible inert products, introduced as impurities of the reagents fed or present in the passivation air, when this is used, are discharged through line 11 leaving the condenser C and preferably fed to the section P for recovering the ammonia still possibly present in the mixture.

The separation and purification section of urea P, comprises a complex combination of apparatuses, which is not shown in detail in FIG. 1, for the decomposition of the ammonium carbamate and separation of the non-converted reagents and water, still present in the semi-purified liquid mixture leaving the stripper S, which is fed through lines 7 and 9 between which the exchanger F is interposed, and also for the purification and/or solidification of the urea. The urea produced, through line 14, the blowdown water, from line 15, the two streams carried by lines 1 and 2, previously described, and the blowdown stream 16 of the purified inert products I, are therefore obtained from the section P.

With reference to FIG. 1, some possible preferred embodiments of the process of the present invention are now described, even if this description is not limitative of the overall scope of the invention itself.

Fresh ammonia, fed through line 13, is compressed and joined with that recovered in the section P, and the resulting stream sent to the reactor R through line 1, the ejector E, where it exerts the function of driver, and the subsequent line 4, which therefore also comprises the stream of ammonium carbamate with a reduced water content, coming from the condenser of the carbamate C. It is also possible, according to a variant of the process according to the present invention, not shown in FIG. 1, that the ammonia be fed, totally or partially, to the stripper S, to further favour the entrainment of gases separated.

Under the normal operating conditions of the process according to the present invention, the stream 1 prevalently contains ammonia in the liquid state.

After compression to 14-18 MPa, all the fresh $CO_2$ is preferably sent to the reactor R through line 3, but according to other embodiments of the present invention, not shown in FIG. 1, can be sent, for example, for more than 50% to the reactor and the remaining part to the condenser C, to regulate the enthalpic requirements of the reactor, or in part be also sent to the stripper S, in which case it is also used as stripping means or as a carrier stream of passivating agents such as oxygen or hydrogen peroxide, according to what is known in the art.

Preferably at least 80%, more preferably at least 95%, of the fresh carbon dioxide, after compression, is sent to the reactor, and the remaining part fed to the condenser C.

The overall feeding of the reactor consists of streams 3 and 4, the latter with a very limited water content, partly deriving from the possible formation of urea already in the condenser of ammonium carbamate C. According to the present invention, the reactor thus preferably operates with an overall feed in which the molar ratio between water and $CO_2$ is lower than 0.4.

The liquid stream 5 discharged from the reactor R by means of the overflow T, containing urea, water, ammonia and ammonium carbamate, is fed to the head of the stripper S, together with the stream carried by line 8, containing at least 50%, preferably from 80 to 100% of said fourth liquid mixture of step (d). The part of said fourth liquid mixture possibly remaining is removed through the valve V2 and sent to the condenser C, either directly (option not shown in FIG. 1), or through line 12, which flows into line 6.

The part of said fourth liquid mixture fed to the stripper S at the operating pressure of the synthesis loop of urea, is brought to a temperature more preferably ranging from 160 to 210° C. in the exchanger F, by thermal exchange between the stream coming from P and fed through line 2 at a temperature ranging from 70 to 100° C., and stream 7, consisting of the second liquid mixture leaving the stripper S at a temperature ranging from 180 to 220° C.

According to the present invention, the heat exchanger F which can be used for preheating the fourth liquid mixture coming from the section P, is preferably a surface exchanger of the tube-bundle and shell type. In this exchanger, the fluids to be treated pass respectively through the tubes collected inside a cylindrically-shaped container or in the surrounding space, called shell. Experts in the field are free to choose which fluid is to be sent into the shell or into the tubes respectively.

In a typical tube-bundle and shell exchanger, the following parts can be distinguished in particular:
  the end heads (rear head and front head) that delimit the volume consisting of the internal part of the tubes and which is called tube side.
  the tubes themselves which are fixed to a very thick perforated sheet called tube plate. The coupling between tubes and tube bundle can be effected by "flaring" and subsequent welding or by means of threading.
  the outer casing (or shell), which delimits the external volume of the tubes, called shell side.

Two flanged gates reserved for the fluid to be heated are associated with the shell, whereas the two end heads each have a single flanged gate reserved for the fluid to be cooled.

Transversal sheet plates called diaphragms are preferably present in the shell, whose purpose is to control the hydraulic regime in the shell itself.

In said exchanger F, the fluid of stream 7 preferably enters the tube side of the exchanger and is cooled by heating the solution of stream 2, which preferably enters the shell side and is heated. The heat exchange preferably takes place in countercurrent.

The stream 2 leaving P, which carries said fourth recycled liquid mixture, is sent, through the pump not shown in FIG. 1, at a pressure substantially equal to that of the stripper S and the whole synthesis loop, according to what is customary in the known synthesis processes of urea of the total recycling type. The exchanger F consequently operates with tube-side and shell-side fluids substantially at the same pressure and does not require tubes have a considerable thickness, increasing the efficiency of the thermal exchange.

As it is in contact with fluids which are potentially highly corrosive, the exchanger F is preferably made of valuable materials, stainless steel, titanium or zirconium, or a combination of these, more preferably, for reasons of lower cost, it is made of 25.22.2 Cr.Ni.Mo stainless steel. The outer force body, necessary for sustaining the high pressure inside the exchanger, is generally made of carbon steel having an adequate thickness, according to the project specifications, internally coated with one or more of said valuable materials.

According to a possible variant of the process of the present invention, not shown in FIG. 1, the gaseous phase possibly present at the head of the reactor R, instead of being sent in line 5 in a mixture with the liquid, can be removed separately from the head of the reactor and sent, either totally or partially, to the bottom of the stripper S, with the function of either entrainment gas, to favour the decomposition-stripping in step (b), or passivation agent of the metallic surfaces exposed to corrosion, as it contains traces of oxygen possibly introduced with the feeding of $CO_2$. This variant is known to experts in the field and analogously described, for example, for a different synthesis method of urea, in European patent application EP 751121.

The gaseous stream discharged from the head of the stripper S, containing $NH_3$ and $CO_2$ and having a low water content, preferably lower than 15% by weight, and more preferably ranging from 2 to 10% by weight, is sent to the condenser C through line 6. Here it is condensed, at a similar pressure or slightly lower than that of the reactor and at the highest temperature possible, preferably higher than 150° C., to obtain a liquid stream (third liquid mixture) prevalently containing ammonium carbamate and ammonia, in addition to smaller quantities of water and possibly urea. The latter can be formed during the condensation step as the lower quantity of water present creates operative conditions favourable for partially shifting the chemical equilibrium (1b) previously indicated, towards the right. The liquid stream thus obtained is fed to the reactor R through line 10 and the ejector E.

EXAMPLE

In order to further illustrate the objective and advantages of the present invention, a practical example is provided hereunder which, however, in no way represents a limitation of the scope of the claims.

In the practical embodiment example, the compositions of the different streams are given with reference to the base components, urea, ammonia, carbon dioxide and water, regardless of whether the carbon dioxide, in the high-pressure liquid streams containing free ammonia, is substantially in the form of ammonium carbamate.

A process for the synthesis of urea according to the present invention, operates by feeding the recovery stream coming from the separation and purification section of urea P, to the stripper S, after being preheated in the exchanger F. Reference is made to the scheme shown in FIG. 1.

741 kg/h of fresh $CO_2$ (containing 8 kg/h of inert products) and 300 kg/h of recycled $CO_2$ in the form of ammonium carbamate are respectively fed to the reactor R from lines 3 and 4. Stream 4 also contains 1517 kg/h of ammonia (free or as ammonium carbamate) and 75 kg/h of water. This water content is greatly reduced, in proportion, with respect to normal total recycling processes known in the art.

The reactor operates at 15.5 MPa and 190° C. with an N/C ratio=3.8 and a H/C ratio=0.18.

The liquid stream 5 discharged from the overflow T of the reactor, which contains the whole urea produced and forms said first liquid mixture having a temperature of 190° C., is characterized in particularly by the following flow-rates:

Urea=1000 kg/h
$H_2O$=375 kg/h
$CO_2$=300 kg/h
$NH_3$=950 kg/h
Inert products=8 kg/h The conversion (moles of urea produced/moles of $CO_2$ fed) obtained in the reactor is 71%.

The stream 5 flows together with stream 8, coming from the urea purification and concentration section P, through the heat exchanger F, where it is brought to a temperature of 200° C., said stream containing all the recycled ammonium carbamate from the medium- or low-pressure separation steps. On the whole, the resulting stream fed to the head of the stripper S at a temperature T=193° C., consists of:

Urea=1000 kg/h
$H_2O$=573 kg/h
$CO_2$=418 kg/h
$NH_3$=1292 kg/h
Inert products=8 kg/h The stripper S operates at about 15 MPa, at a bottom temperature of 208° C., without the introduction of stripping gas, but using the same ammonia vaporized from the liquid, wherein there is a large excess, as entrainment gas (so-called self-stripping mode). The energy supplied to the stripper by means of saturated vapour at a pressure of 21 MPa is about 200 $Kcal/kg_{urea}$.

A gaseous stream 6 (first gaseous stream) is discharged from the head of the stripper S, containing a minimum amount of water and characterized by the following composition:

$NH_3$=777 kg/h
$CO_2$=303 kg/h
$H_2O$=75 kg/h
inert products=8 kg/h

A liquid stream 7 is discharged from the bottom of the stripper, at a temperature of 208° C., consisting of:

Urea=1000 kg/h
$NH_3$=515 kg/h
$CO_2$=115 kg/h
$H_2O$=498 kg/h which is sent to the exchanger F as heating fluid, and subsequently, through line 9, to the purification and concentration steps of urea in the section P.

The condenser C receives the gaseous stream 6 and, operating at pressures of about 15 MPa and a temperature of 155° C., according to the normal operating conditions of total recycling processes known in the art, returns a liquid stream (third liquid stream) containing ammonium carbamate and ammonia with a small amount of water, which is fed to the reactor R by means of line 10, the ejector E and line 4, in sequence. Under these temperature and pressure conditions, there is no formation of solids by crystallization. The condenser consists of a tube-bundle apparatus of the Kettle type, with the removal of heat by the formation of medium- or low-pressure vapour, in the shell.

A gaseous stream 11 is collected from the head of the condenser C, said stream containing the inert products (8 kg/h) diluted in a small amount of ammonia (50 kg/h) and $CO_2$ (3 kg/h) which is sent to the same purification and concentration section of urea P for the definitive separation of the inert products I, which are flushed from line 16.

The ejector E receives, from the section P, a substantially pure liquid ammonia stream through line 1, having a flow-rate of 790 kg/h, which contains all the fresh ammonia feed and an aliquot of recycled ammonia. This ammonia stream in compressed (by means of a pump not shown in FIG. 1) to a pressure slightly higher than that of the reactor so that it can be used as driving fluid of the mixture coming from the condenser C through line 10, having the following composition:

$NH_3$=727 kg/h
$CO_2$=300 kg/h
$H_2O$=75 kg/h thus forming the feeding stream 4 to the reactor R.

The purification and concentration section of urea P comprises, in this particular case, the typical medium- and low-pressure separation sections, and the concentration section characterizing the traditional Snamprogetti Urea Process, whose general scheme is indicated, for example, on page 612 of the publication "Encyclopaedia of Chemical Technology" mentioned above, and whose constructive and process details are not relevant however for illustrating the present invention.

1,000 kg/h of pure urea are recovered from the section P by means of line 14 together with 300 kg/h of water from line 15, whereas 567 kg (h of fresh ammonia are fed through line 13. Furthermore, a stream 2 (fourth liquid stream) of recycled ammonium carbamate, having the following composition:

$NH_3$=342 kg/h
$CO_2$=118 kg/h
$H_2O$=198 kg/h is obtained from the section P, in addition to stream 1 of liquid ammonia mentioned above.

The mixture leaving P by means of line 2 has a temperature of 90° C., and before being fed to the stripper S together with stream 5, is subjected to heating to 200° C. (line 8) by heat exchange in the exchanger F with stream 7 coming from the bottom of the stripper at 208° C., which is cooled to 150° C. and is sent, through line 9 and the depressurization valve V1, to the separation and purification of urea in section P. The heat exchanger F operates in countercurrent by passing the hot stream coming from the stripper S to the tube side, and the recycled stream leaving the section P to the shell side. The exchanger used is of the single passage type, as, for both the tube side and shell side, the fluids pass through the exchanger only once. In the case illustrated, the exchanger F is made of stainless steel 25.22.2 Cr.Ni.Mo and equipped with 20 tubes having a length of 6 m and a diameter of 150 mm. The tubes are welded directly onto the tube plate.

The process for the synthesis of urea exemplified above is characterized by a conversion of $CO_2$ to urea, i.e. the molar ratio (urea produced)/($CO_2$ fed to R)×100, equal to 71%. This value, which is higher than what is normally obtained in the total recycling industrial processes known in the art, is in line with the conversion value (73%) of the process described in the cited European patent nr. 727414. According to the present invention, however, the synthesis process can be effected with a much more versatile control of the heat level of the stripper, with the possibility in particular—especially when the process is carried out in a plant obtained by the revamping of a pre-existing plant—of using the same decomposition and stripping equipment with no risks of blockage and overflow. In the absence of heat exchange which characterizes the present invention, a process analogous to that exemplified above requires a stripper having an exchange surface about 30% larger.

Numerous variations or modifications of the process described above are obviously possible, which should however be considered as being fully included in the scope of the present invention.

The invention claimed is:

1. A process for the synthesis of urea from ammonia and carbon dioxide with the formation of ammonium carbamate as intermediate, comprising the following steps:
 (a) reacting ammonia and carbon dioxide as such or in the form of ammonium carbamate, with a $NH_3/CO_2$ molar ratio ranging from 2.3 to 6, at temperatures ranging from 140 to 215° C. and pressures ranging from 12 to 25 MPa, with the formation of a first liquid mixture containing urea, ammonium carbamate, water and ammonia;
 (b) feeding said first liquid mixture to a decomposition-stripping step to effect the decomposition of at least an aliquot of the ammonium carbamate into ammonia and carbon dioxide, operating at the pressures of said reaction step (a) and at temperatures ranging from 160 to 240° C., simultaneously subjecting said liquid mixture to stripping with the formation of a first gaseous mixture containing ammonia and carbon dioxide, and a second liquid mixture containing urea, water, ammonia and ammonium carbamate:
 (c) condensing at least 50% of said first gaseous mixture in a condensation step, operating at the pressures as said step (a), with the formation of a third liquid mixture containing ammonium carbamate, ammonia and possibly urea, fed to the reaction step (a);
 (d) recovering the urea contained in said second liquid mixture in one or more consecutive decomposition and separation steps (P), with the formation of a fourth liquid mixture containing water, ammonia and ammonium carbamate and, possibly, a liquid phase containing ammonia;
 (e) feeding at least an aliquot of said fourth liquid mixture formed in step (d) to said decomposition-stripping step (b), sending the part possibly remaining to said reaction step (a), or to said condensation step (c);
 wherein said fourth liquid mixture totally or partially fed to said decomposition-stripping step (b), is preheated by thermal exchange with any of the above mixtures formed in steps (a), (b) or (c).

2. The process according to claim 1, wherein said fourth liquid mixture is preheated by thermal exchange with said first gaseous mixture, or said second liquid mixture formed in step (b).

3. The process according to claim 1, wherein said $NH_3/CO_2$ ratio in the reactor ranges from 3.0 to 5.0.

4. The process according to claim 1, wherein said reaction step (a) is carried out at temperatures ranging from 170 to 205° C. and pressures ranging from 14 to 18 MPa.

5. The process according to claim 1, wherein said decomposition-stripping step (b) is carried out at temperatures ranging from 180 to 220° C. under self-stripping conditions.

6. The process according to claim 1, wherein the initial temperature of said fourth liquid mixture ranges from 70 to 120° C. and the temperature variation during the preheating ranges from 30 to 140° C.

7. The process according to claim 1, wherein the initial $H_2O/CO_2$ molar ratio in said reaction step (a) ranges from 0.10 to 0.35.

8. The process according to claim 1, wherein said fourth preheated liquid mixture is joined with said first liquid mixture before being fed to the decomposition-stripping step (b).

9. The process according to claim 1, wherein said fourth liquid mixture represents from 25 to 35% by weight with respect to said second liquid mixture.

10. The process according to claim 1, wherein said liquid phase containing ammonia produced in step (d) is fed, as recycling, to said reaction step (a).

11. A method for enhancing the yield of an existing process for the production of urea, which operates with a high-pressure synthesis section comprising at least one (self)stripping step from which a liquid stream containing urea and a gaseous stream containing ammonia and carbon dioxide are obtained, and subsequent purification and concentration steps of urea, from which a recycled aqueous solution containing ammonium carbamate is obtained, wherein said aqueous solution is fed, totally or partially to said (self)stripping step wherein said aqueous solution is preheated by thermal exchange with said liquid stream containing urea or said gaseous stream, before being fed, either totally or partially, to said (self)stripping step.

* * * * *

UNITED STATES PATENT AND TRADEMARK OFFICE
CERTIFICATE OF CORRECTION

PATENT NO.        : 8,927,770 B2  
APPLICATION NO.   : 14/116258  
DATED             : January 6, 2015  
INVENTOR(S)       : Lino Carlessi and Alessandro Gianazza Page 1 of 1

It is certified that error appears in the above-identified patent and that said Letters Patent is hereby corrected as shown below:

Title Page, (73) Assignee: change "Salpem S.p.A." to --Saipem S.p.A.--

Signed and Sealed this  
Twenty-seventh Day of October, 2015

Michelle K. Lee  
*Director of the United States Patent and Trademark Office*